United States Patent [19]

Holman et al.

[11] 4,456,589
[45] Jun. 26, 1984

[54] PREPARATION OF ANIMAL TISSUES FOR SURGICAL IMPLANTATION IN HUMAN RECIPIENTS

[75] Inventors: Daniel G. Holman, Blaine; Arthur A. Beisang, Roseville, both of Minn.

[73] Assignee: Genetic Laboratories, Inc., St. Paul, Minn.

[21] Appl. No.: 396,416

[22] Filed: Jul. 8, 1982

[51] Int. Cl.$^3$ .............................................. A61K 35/12
[52] U.S. Cl. ..................................................... 424/95
[58] Field of Search ......................................... 424/95

[56] References Cited
PUBLICATIONS

Im et al.—Chem. Abst., vol. 77, (1972), p. 162957j.
McMaster et al.—Chem. Abst., vol. 85, (1976), p. 51707y.
Shamatov et al.—Chem. Abst., vol. 79, (1973), p. 87947s.

Primary Examiner—Sam Rosen
Attorney, Agent, or Firm—Orrin M. Haugen; Thomas J. Nikolai; Douglas L. Tschida

[57] ABSTRACT

A process for treating animal tissue to make it acceptable for implantation in a human recipient without rejection or reabsorption, the process including the step of tanning the cartilage chemically or by irradiation: a preliminary dehydration step and a subsequent step of storage in an anti-microbial medium may also be used.

20 Claims, No Drawings

PREPARATION OF ANIMAL TISSUES FOR SURGICAL IMPLANTATION IN HUMAN RECIPIENTS

TECHNICAL FIELD

This invention relates to the field of surgery, and more particularly to procedures for treating animal tissues to make them acceptable as surgical implants in human recipients.

BACKGROUND OF THE INVENTION

The use of tissue implants in surgery on human patients has been known for some time. Implants using cartilage from a human source have been successful, but there is some history of rejection by the patient's body when the tissue is from some other animal.

BRIEF SUMMARY OF THE INVENTION

The present invention comprises procedures for treating animal cartilage such as may be harvested from slaughtered livestock so that it is accepted rather than rejected and so that it retains its original shape on implant rather than twisting or altering its shape after implant in human subjects such that it may be used in plastic or reconstructive surgery. Because of the treatment, implant site infections will be minimized due to the release of silver ions from the implanted tissue. The present invention also describes a procedure for treating animal pericardium so that it is accepted rather than rejected by human subjects for aorta patches and heart shields. Again because of the manner in which the pericardium is pre-treated, the occasion of implant site infection is greatly reduced. The procedures use one or more of the following steps: dehydration of the animal tissue; tanning the tissue chemically or radiatively; and storing of the treated tissue in an anti-microbial medium including propylene oxide or silver ions.

Various advantages and features of novelty which characterize the invention are pointed out with particularity in the claims annexed hereto and forming a part hereof. However, for a better understanding of the invention, its advantages, and objects attained by its use, reference should be had to the accompanying descriptive matter, which gives details of certain preferred embodiments of the invention.

DESCRIPTION OF PREFERRED PROCEDURES

The invention will first be described as applied to the processing of cartilaginous tissue. Fresh animal costal and nasal cartilage is harvested within one hour of slaughter from choice grade cattle or other livestock aged 12 to 24 months. A clean, sharp knife is utilized to neatly trim nasal cartilage from the skull of the animal, or costal cartilage from beneath the animal's brisket. The harvested cartilage is immediately placed in a cooler with wet ice for transportation to the production laboratory. Here each piece of the cartilage is cleaned of all attached tissue and all attached fat, using a clean, sharp scalpel, so that the cartilage piece appears clean and white.

Each fresh cartilage piece is cut to provide implants of suitable size for certain standard operative procedures: for example, a "nose blank" may be 40 to 50 millimeters in length, 5 to 15 millimeters in width, and 4 to 6 millimeters in thickness. The cuts are made to obtain the most useful material from each cartilage. If desired, selected pieces of the cartilage after cleaning may be formed into a "compound graft" using wire, sutures, or glues. A representative piece of each original cartilage is also cut as a control section, and samples are taken for culture preparation to confirm sterility of the completed implants.

The sized pieces, grafts, samples, and control sections are next placed in individual plastic pouches containing normal physiological saline solution, and are heat sealed. The pouches are placed in boxes and irradiated with beta or gamma radiation at a level of 3.0 Mrad, which has a tanning and sterilizing effect on the material. After radiation, the sized pieces, grafts, and control sections are placed in quarantine freezer storage, and the samples are subjected to a culture procedure to verify sterility.

If visual growth is observed in the culture test during a 14-day incubation period, the quarantined material is discarded. If no growth is observed, the quarantined material is considered sterile, removed from quarantine freezer, and placed in inventory. The pouched material may be stored at room temperature without deterioration.

Alternative procedures for tanning and sterilizing the animal tissue are also available. Tanning can be accomplished chemically using glutaraldehyde, as will now be explained, applied to pericardial tissue. After harvesting from freshly slaughtered animals such as bovines, the pericardial sacs are stored in plastic bags in a freezer for transportation to the production laboratory. Here the bags are thawed in cool tap water, the sacs are removed and stored temporarily in sterile 0.9 percent saline solution until they can be cleaned by pushing or cutting away adipose tissue from the fibrous, translucent pericardium itself. After being rinsed in sterile 0.9 percent saline solution and lightly squeezed to remove excess, the pericardium is submerged in 95 percent ethanol for at least 72 hours. It has been found that the resulting dehydration of the pericardium has a beneficial effect in improving the tanning step which follows.

The sac is removed from the ethanol, rinsed with sterile deionized water, and submerged in 0.25 percent glutaraldehyde solution for at least 48 hours to accomplish the desired tanning. After rinsing and short soaking in saline solution, the sac is stored in a sterilant comprising one part by volume of propylene oxide solution and 99 parts by volume of 70 percent ethanol—73 parts of 95 percent ethanol with 27 parts of deionized water. The sac may be stored in sterilant at room temperature.

The pericardial tissue is most useful as "patches" 4×6 centimeters or 10×10 centimeters, and as "shields" 6×15 centimeters. Each sac is accordingly reduced to portion of these sizes, after which the patches or shields are wound individually on sterile Teflon mandrels and stored in sterilant in appropriate glass tubes at room temperature.

As an alternative tanning procedure, dialdehyde starch may be substituted for glutaraldehyde. As a further alternative, the storage solution may comprise a silver ion containing chemicals such as silver nitrate or silver sulfadiazine. When so treated, the collagen in the pericardium associates with the silver ion containing chemicals, which silver ions are released out of the patch or shield over a period of time so as to prevent infection by killing microbes.

From the foregoing it will be evident that the invention comprises procedures for treating animal tissues by tanning and sterilization, which makes the tissues acceptable in the body of a human recipient without rejection or reabsorption.

Numerous characteristics and advantages of the invention have been set forth in the foregoing description, together with details of the method and function of the invention, and the novel features thereof are pointed out in the appended claims. The disclosure, however, is illustrative only, and changes may be made in detail, especially in matters of sequences, times, concentrations, etc. within the principle of the invention, to the full extent indicated by the broad general meaning of the terms in which the appended claims are expressed.

We claim

1. The method of preparing animal cartilage for implant use in plastic or reconstructive surgery on human subjects which includes the step of chemically tanning cleansed, dehydrated cartilage.

2. The method of claim 1 in which the tanning agent is glutaradehyde.

3. The method of claim 1 in which the chemical agent is dialdyhyde starch.

4. The method of claim 1 including the further step of rinsing the tanned material in saline solution and storing it in an anti-microbial medium made up of ethanol and propylene oxide.

5. The method of claim 4 in which the anti-microbial medium comprises 99 parts by volume of 70% ethanol and one part by volume of propylene oxide.

6. The method of treating animal tissue which has been freed of adipose tissue, comprising the steps of:
    (a) dehydrating the tissue by immersion for at least 72 hours in 95% ethanol;
    (b) rinsing the tissue in sterile deionized water;
    (c) tanning the tissue by immersion for at least 48 hours in 0.25% glutaraldehyde;
    (d) rinsing the tissue in 0.9% saline solution; and
    (e) storing the tissue at room temperature in an anti-microbial medium of 99 parts by volume of 70% ethanol and 1 part by volume of propylene oxide.

7. The method of treating animal tissue which has been freed of adipose tissue, comprising the steps of dehydrating the tissue, first rinsing the tissue, tanning the tissue, again rinsing the tanned tissue, and storing the tanned tissue at room temperature.

8. The method of claim 7 in which the tissue is nasal cartilage.

9. The method of claim 7 in which the tissue is costal cartilage.

10. The method of claim 7 in which the tissue is pericardium.

11. The method of claim 7 in which the dehydration is accomplished by immersion in 95% ethanol.

12. The method of claim 7 in which the dehydration is accomplished by immersion for at least about 72 hours in 95% ethanol.

13. The method of claim 7 in which the tissue is first rinsed in sterile deionized water.

14. The method of claim 7 in which the tissue is rinsed in sterile 0.9% saline solution.

15. The method of claim 7 in which the tissue is stored in saline solution.

16. The method of claim 7 in which the tissue is stored in an anti-microbial medium.

17. The method of claim 16 in which the anti-microbial medium is 99 parts by volume of 70% ethanol and 1 part by volume of propylene oxide.

18. The method of claim 16 in which the anti-microbial medium includes a source of silver ions.

19. The method of claim 18 in which the anti-microbial medium includes silver nitrate.

20. The method of claim 18 in which the anti-microbial medium includes silver sulfadiazine.

* * * * *